United States Patent [19]

Holever

[11] 4,240,417
[45] Dec. 23, 1980

[54] TRACHEAL TUBE ADAPTER FOR VENTILATING APPARATUS

[76] Inventor: Bernard K. Holever, 241 Cottonwood Rd., Newington, Conn. 06111

[21] Appl. No.: 48,095

[22] Filed: Jun. 13, 1979

[51] Int. Cl.³ .............................................. A61M 16/00
[52] U.S. Cl. ........................ 128/203.12; 128/207.15; 128/912
[58] Field of Search ...................... 128/207.14, 207.15, 128/207.16, 912, 349 B, 349 BV, 204.18, 200.18, 200.21, 203.12

[56] References Cited

U.S. PATENT DOCUMENTS

| | | | |
|---|---|---|---|
| 3,172,406 | 3/1965 | Bird et al. | 128/200.18 |
| 3,730,179 | 5/1973 | Williams | 128/204.18 |
| 3,731,691 | 5/1973 | Chen | 128/207.15 |
| 4,030,492 | 6/1977 | Simbruner | 128/200.21 |
| 4,045,058 | 8/1977 | Eross | 128/207.14 |

Primary Examiner—Henry J. Recla

Attorney, Agent, or Firm—McCormick, Paulding & Huber

[57] ABSTRACT

A conventional ventilating apparatus is connected to the projecting end of a breathing tube inserted through a tracheostomy opening into the patient's throat with an inflatable cuff at the lower end of the tube to seal the patient's throat. An adapter is provided to connect the ventilating apparatus to the tracheal tube. A port is defined in the adapter, opposite the portion of the adapter for connection to the tube, such that removal of a plastic cap permits insertion of a vacuum tube for withdrawing excessive fluid from the patient's lungs. The ventilating apparatus connects with the adapter through a side opening port and this disclosure relates particularly to still another port provided for connecting the tracheal tube to a source of lubricating fluid for purposes of injecting a saline solution or other lubricant into the patient's lungs when required to relieve dryness in the patient's lungs. This last mentioned port also includes a one-way check valve which enables medicant or saline to be inserted to loosen tenacious secretions under a pressurized closed system.

4 Claims, 3 Drawing Figures

TRACHEAL TUBE ADAPTER FOR VENTILATING APPARATUS

SUMMARY OF THE INVENTION

This invention relates generally to ventilating apparatus for patients who have had a tracheostomy operation to permit a tracheal tube to be inserted into the neck, and into the throat, so that breathing through the mouth is not required, and the patient's lungs are instead cyclically ventilated from a mechanical contrivance of conventional design. More particularly this invention relates to an adapter for use on the outer end of the tracheal tube for connecting the patient's throat to such a ventilating apparatus, and for permiting insertion of a vaccum tube or the like to relieve conjestion in the patient's lungs by evacuating the lungs as required, which adapter further includes a third port for connecting the tracheal tube to a source of lubricating fluid such as a saline solution or other medicant. Although this third port might be selectively connected to such a source, it will be apparent that this invention also contemplates a permanent connection with such a source.

Heretofore, adapters of the type used to connect a ventilating apparatus to a tracheal tube have required that a removable cap cover the single port normally provided for selectively connecting the tracheal tube to such a source of lubricating fluid, and alternatively for permitting insertion of a vacuum tube for removal of excess moisture in the patient's lungs. Such prior art adapters suffer from the disadvantage that when inserting the medicant, the patient is apt to cough up the lubricating fluid when introduced through such an open port.

The present invention seeks to obviate this disadvantage as a result of providing a port specifically designed to permit the introduction of such a lubricating fluid without involving the normally closed port through which a vacuum tube or the like is normally inserted.

The injection of saline or medicant via such a port in the ventilation adapter is very effective in relieving lung dryness, and also in loosening tenacious secretions residing in the patient's lungs.

DETAILED DESCRIPTION

Figure 1:
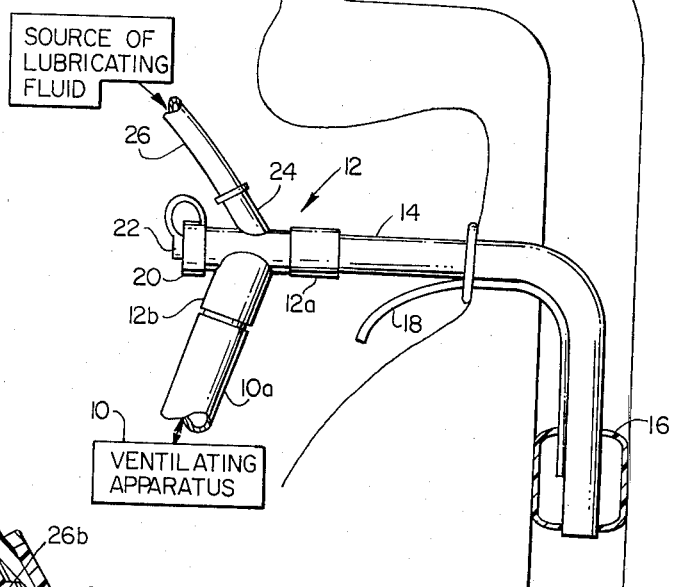
FIG. 1 is an elevational view showing in schematic fashion a patient with a tracheal tube inserted through a tracheostomy opening in his neck, and illustrates the adapter of the present invention provided with suitable connections to a source of lubicating fluid and to the conventional ventilating apparatus normally provided for operating the patient's lungs.

Turning now to the drawing in greater detail, FIG. 1 shows a patient connected to a conventional ventilating apparatus 10 such that oxygenated air can be introduced into the patient's lungs through an adapter 12, and through a tracheal tube 14 provided in an opening in the patient's throat and having a inner end portion equipped with a cuff 16 of conventional construction adapted to be inflated after insertion of the tracheal tube through the line 18. A patient so equipped can be caused to breathe normally as a result of the cyclically operating ventilating apparatus 10, which periodically introduces fresh air to the lungs and withdraws the stale air according to a preestablished timing control of conventional construction. Patients connected to such a ventilating apparatus for long periods of time can suffer from dryness of the lungs, and the adapter 12 preferably has an opening or port 19 defined at its forward end, which opening is normally covered by the cap 20. The cap 20 is so designed that it can be removed, or the smaller portion 22 swung open in order to provide entrance for a nebulizer or other moisture spraying aerosol device (not shown) as required to introduce a saline solution, in mist form, or some other medication in the form of a lubricating fluid in order to relieve the dryness associated with long periods of use or connection with a ventilating apparatus such as shown at 10 in FIG. 1.

The disadvantages to introducing a moisturized liquid solution through the port 19 defined at the forward end of the adapter 12 are related to the fact that upon introduction of such fluids into the patient's lungs the patient is apt to cough and to expell not only the fluids so introduced, but also germ laden fluids residing in the lungs themselves. In order to overcome this disadvantage I have provided another port in the form of the means 24 on adapter 12 such that this portion of the adapter can be used to introduce such lubricating fluids into the patient's lungs.

The additional port defining means 24 provided for this purpose will be seen to permit the conventional forwardly opening port 19 covered by the plastic cap 20 to be used for the introduction of a vacuum tube or the like in order to suck out undesirable amount or quantities of moisture from the patient's lungs.

Figure 2:
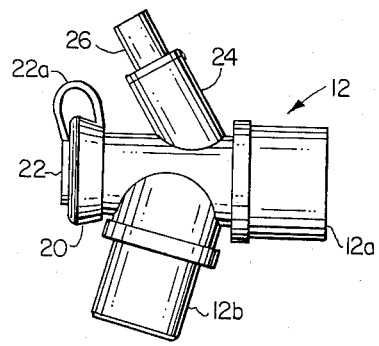
FIG. 2 is an elevational view of the adapter depicted in FIG. 1, but drawn to a slightly larger scale.

By way of summary then my invention relates to the environment of a patient ventilating apparatus which includes conventional apparatus for cyclically causing the patient to inhale and to exhale through a tracheal tube inserted through a tracheostomy opening into his throat. The lower end of the tracheal tube is held in the throat by an inflatable cuff 16, and the upper end of the tube projects forwardly through the tracheostomy opening for receiving my improved adapter 12. The adapter itself comprises a plastic part with several ports defined in it, one for receiving the end of the tracheal tube, and an axially opposed opening 19 which is normally covered by a cap, such as shown at 20 in FIG. 1. The cap may include a closable lid 22 with the lid having a self-hinge 22a connected to the plastic closure portion 20 as better shown in FIGS. 2 and 3. This port 19 is provided opposite the port defining means 12a for receiving the tracheal tube and allows opening of the cover 22 and insertion of a vacuum tube (not shown) in order to withdraw undesirably high quantities of moisture in the patient's lungs should this be necessary after prolonged use, or the patient's connection with, the ventilating apparatus 10. Normally, such prolonged connection of a patient to a ventilating apparatus will cause dryness in the lungs, and therefor an aerosol mist must sometimes be injected through the opening 19 referred to above. However, when a lubricating fluid or moisturizer is so introduced the patient is apt to cough or spit material from within his lungs, and when the mist is introduced through the opening 19 some of this noxious material will be ejected into the atmosphere and perhaps into the face of the technician administering the medicant.

Figure 3:
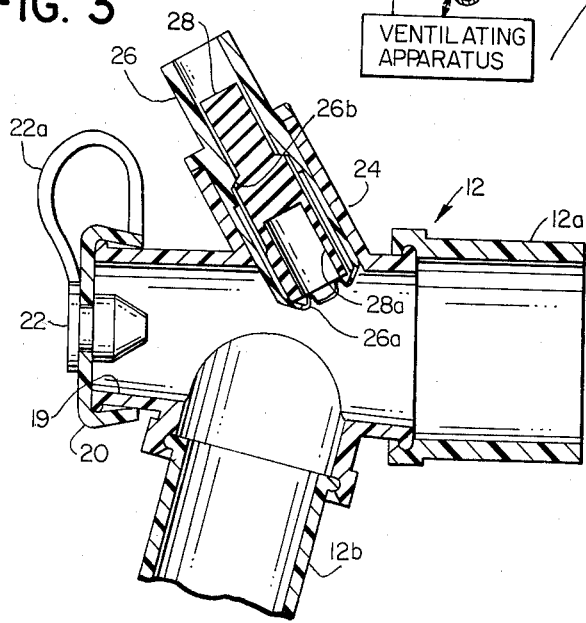
FIG. 3 is a sectional view through the adapter illustrated in FIG. 2.

In accordance with my invention an additional port is defined by means 24 on the adapter for selectively connecting the tracheal tube 14 to a source of lubricating fluid such that these materials will not be ejected into the atmosphere. Referring now to FIG. 3 in greater detail the adapter 12, and particularly the portion 24 for communication with the source of lubricating fluid or medicant will now be described in greater detail.

The adapter 12 is preferably cast from plastic or the like, and may include a nipple 12a for convenient connection to the tracheal tube 14 in such a manner as to permit swiveling of the entire adapter on the axis of the upper end of the tube 14. The adapter 12, and more particularly the rotary nipple 12a, provides a convenient means defining a tracheal tube port suitable for receiving or being received on the forwardly projecting end portion of the tracheal tube 14. The adapter 12 also includes a connection, or port defining means 12b also formed as a rotary nipple, for receiving the conduit 10a from the ventilating apparatus 10, and this respiratory port defining means oriented at a substantial angle with respect to the above mentioned tracheal tube port 12a so that the above described open port 19 which is normally closed by the cover 20, is defined in axial alignment with the tracheal tube port 12a in order to permit insertion of a vacuum tube or the like (not shown) for withdrawing liquids from the patient's lungs.

The adapter 12 also includes means 24 defining a third port for the selective injection of a lubricating fluid other than through the open end port 19, and since such a third port need not necessarily be aligned with the axis of the tracheal tube port 12a I have provided this third port in an inclined boss in the adapter 12, which boss is suitable for housing a one way check valve means for normally closing this port, but adapted to be opened under pressure in the line 26 such that fluid under pressure in a mist form can be provided from a nebulizer or the like in order to relieve dryness in the patient's lungs. The check valve means comprises a plastic valve body 26 and a soft elastomeric valve element 28 reciprocable within the valve body 26 between the closed position shown, and a valve open position wherein the resilient end portion 28a of the valve element 28 engages the crimped end 26a of the valve body. The entire valve element 28 is preferably formed from the same elastomeric material, but the fact that the less massive portion 28a is held in axial compression by the crimped end 26a of valve body 26 provides an internal force in the valve element tending to urge the element outwardly against the seat 26b, except when fluid pressure is exerted on the outer end of the valve element, urging the valve element inwardly of the boss 24 thereby opening the valve as described in detail in U.S. Pat. No. 3,831,629 issued Aug. 27, 1974 to Mackal et al. The two-piece one-way check valve described in said patent represents my presently preferred valve construction, and is particularly well suited to use in my improved adapter.

The advantage of including a one-way valve is that it maintains a closed system, (between patient and respirator) it enables the injected fluid (saline or medicant) enough time to penetrate, lubricate and loosen tenacious secretions. This maximizes the amount of germ laden material to be suctioned from the lungs thereby enhancing lung function.

Heretofore coventional adapters provided a single port, through which lubricate was instilled. Such adapters suffered from the disadvantage that when lubricant was instilled, the patient spontaneously coughed up the lubricant thru this single port into the atmosphere before it had a chance to lubricate, and loosen secretions in the lungs.

Ideally it is best to remove as many secretions (germs) as possible. This is achieved by allowing lubricate (saline or medicant) to remain in the lungs until proper liquification of secretions occurs. The secretions are then removed via a suction catheter (vacuum).

I claim:

1. An adapter for coupling several different devices to a tracheal tube without disconnecting the patient from a ventilating apparatus, said adapter comprising means defining a chamber and including a tracheal tube port communicating with said chamber and a respiratory port communicating with said chamber oriented at a substantial angle with respect to said tracheal tube port, means defining an opening communicating with said chamber for the insertion of a vacuum tube or the like, removable cap means for selectively closing said vacuum tube opening, means defining a port communicating with said chamber for the selective injection of a lubricating fluid into the tracheal tube, and one-way check valve means in said last mentioned port to prevent the expelling of liquids from the patient's lungs into the atmosphere.

2. An adapter as defined in claim 1 further characterized by said opening being oriented in axial alignment with said tracheal tube port.

3. In a patient ventilating apparatus including ventilating means for cyclically causing the patient to inhale and to exhale, a tracheal tube connected to said ventilating means inserted through a tracheostomy opening into his throat, said tracheal tube having a tracheal cuff mounted on the distal end thereof so that the lower end of the tube is held by the cuff and the upper end projects forwardly through the tracheostomy opening, the improvement comprising an adapter mounted on the projecting end of the tracheal tube, said adapter comprising means defining a chamber and including a tracheal tube port communicating with said chamber and a respiratory port communicating with said chamber oriented at a substantial angle with respect to said tracheal tube port, means defining an opening communicating with said chamber for the insertion of a vacuum tube or the like, which opening is oriented in axial alignment with said trachael tube port, removable cap means selectively closing for said vacuum tube opening, means defining a port communicating with said chamber for the selective injection of a lubricating fluid into the tracheal tube, and one-way check valve means in said last mentioned port to prevent the expelling of liquids from the patient's lungs into the atmosphere.

4. In combination, a tracheal tube adapted for insertion into a tracheostomy opening in a patient's throat, and an inflatable cuff mounted on the distal end of said tracheal tube for sealing the inner end of said tube inside the patient's trachea, an adapter mounted on the outer end of said tracheal tube, said adapter having means defining a chamber and including a tracheal tube port communicating with said chamber for receiving said tube and means defining respiratory port communicating with said chamber oriented at a substantial angle with respect to said tracheal tube port for communication with a patient's lung ventilating apparatus, said adapter having an opening communicating with said chamber opposite said tracheal tube port for receiving a vacuum tube can be inserted axially through said adapter and into said tracheal tube, closure means for selectively closing said opening, boss means defining a port communicating with said chamber for selective communication with a source of lubricating fluid for the patient's lungs, and one-way check valve means in said last mentioned port to prevent the expelling of liquids from the patient's lungs into the atmosphere.

* * * * *